(12) United States Patent
Spenciner

(10) Patent No.: US 8,129,189 B2
(45) Date of Patent: Mar. 6, 2012

(54) FINITE AND MULTIPLE STERILIZATION INDICATION METHOD FOR DEVICES

(76) Inventor: David B Spenciner, North Attleboro, MA (US)

( * ) Notice: Subject to any disclaimer, the term of this patent is extended or adjusted under 35 U.S.C. 154(b) by 239 days.

(21) Appl. No.: 12/209,861

(22) Filed: Sep. 12, 2008

(65) Prior Publication Data

US 2009/0068057 A1    Mar. 12, 2009

Related U.S. Application Data

(60) Provisional application No. 60/971,693, filed on Sep. 12, 2007.

(51) Int. Cl.
*A61L 2/28* (2006.01)
*A61L 2/00* (2006.01)

(52) U.S. Cl. .......... 436/1; 436/2; 422/3; 422/1; 422/50; 422/400

(58) Field of Classification Search .......... 436/1, 2; 422/3, 1, 50, 55, 400
See application file for complete search history.

(56) References Cited

U.S. PATENT DOCUMENTS

| | | | |
|---|---|---|---|
| 7,193,519 B2 | 3/2007 | Root et al. | |
| 2005/0019206 A1* | 1/2005 | Centanni | 422/3 |
| 2006/0134613 A1 | 6/2006 | Martin et al. | |
| 2006/0228801 A1* | 10/2006 | Fryer et al. | 436/10 |
| 2007/0092969 A1 | 4/2007 | Song et al. | |

FOREIGN PATENT DOCUMENTS

| | | |
|---|---|---|
| EP | 0022284 | 1/1981 |
| EP | 0914833 | 5/1999 |
| GB | 2136958 | 9/1984 |
| WO | 2004077002 | 9/2004 |
| WO | 2004114256 | 12/2004 |
| WO | 2006031647 | 3/2006 |
| WO | 2007134006 | 11/2007 |

OTHER PUBLICATIONS

International Search Report and Written Opinion dated Nov. 11, 2008 issued in related International Patent Application No. PCT/US08/76214.
International Preliminary Report on Patentability dated Mar. 25, 2010 issued in related International Patent Application No. PCT/US2008/076214 (5 pages).
Supplemental European Search Report dated Aug. 26, 2010 issued in related European Patent Application No. 08830036.3.
European Communication dated Sep. 14, 2010 issued in related European Patent Application No. 08830036.3.

* cited by examiner

*Primary Examiner* — Christine T Mui
(74) *Attorney, Agent, or Firm* — Grossman, Tucker, Perreault & Pfleger, PLLC

(57) ABSTRACT

The present invention relates to an indicator of sterilization and/or use, which may be affixed to or integrated in a limited use device. The indicator may include a plurality of layers wherein each of the layers includes a membrane. The indictor may also include indicia of the number of uses disposed between the layers. The membranes may breach upon the sterilization or use of the limited use device, wherein the device is exposed to a given environment, such as various gasses, steam, liquids, UV, plasma, etc. In addition, more than one membrane may be provided between each indicia, wherein each membrane may respond to a different environment.

25 Claims, 3 Drawing Sheets

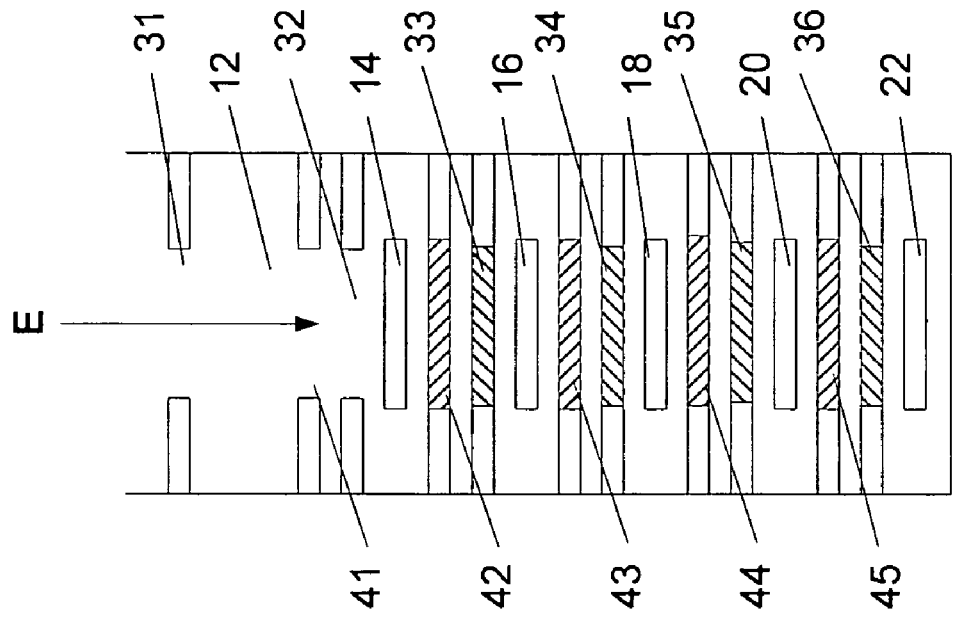
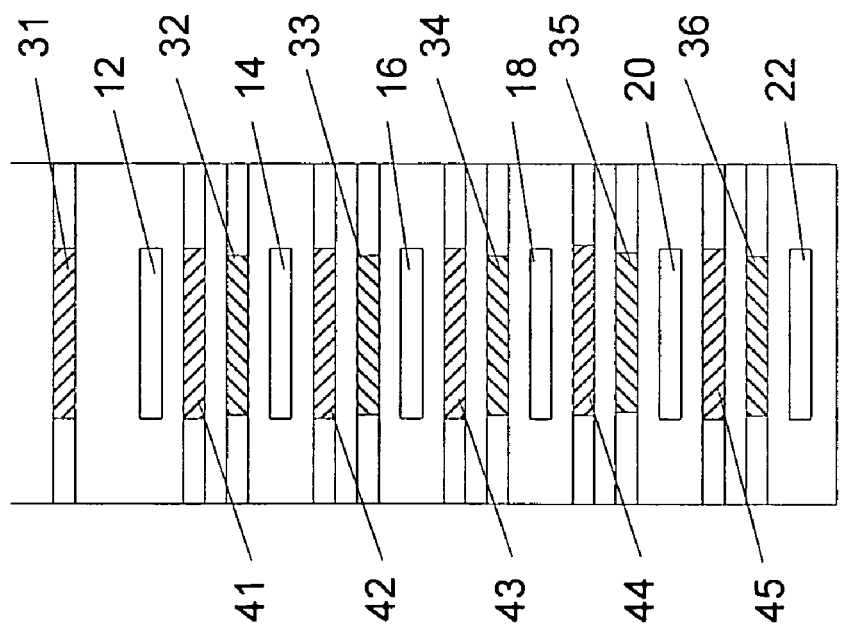

FINITE AND MULTIPLE STERILIZATION INDICATION METHOD FOR DEVICES

CROSS-REFERENCE TO RELATED APPLICATIONS

The present application claims the benefit of the filing date of U.S. Provisional Application 60/971,693 filed on Sep. 12, 2007, the teachings of which are incorporated herein by reference.

FIELD

The present disclosure relates to an indicator for the sterilization of devices, and more specifically, an indicator which may be utilized to indicate multiple sterilization cycles of a limited use device.

BACKGROUND

Many instruments or devices used in the fields of medicine, such as surgical tools, dental devices and veterinary devices require sterilization before use or between uses to prevent harmful bacteria, microbes or other organisms from causing infection. Accordingly, many instruments may be classified into "single use" or "multiple use" categories.

Single use instruments may be provided in a sterile state and are meant to be used for a single patient in a single procedure. In addition, these single use items may be designed such that the device becomes inoperative after their first use to prevent additional uses of the device. An example of a single use device is an inserter for a suture anchor, which may be supplied pre-mounted to the inserter in sterile packaging.

Multiple use items may be used a number of times before they wear out, such that the items may need to be sterilized in between procedures and patients. An example of a multiple use item or device may be a mallet used for hammering. The tool may be used and/or sterilized hundreds or even thousands before the tool is too worn to be re-used.

In other situations a device may be safely reused a limited number of times, but without a proper indicator to represent that the useful life of the tool has expired, re-use may be prohibited. These devices may be categorized as "single use" devices, but would otherwise be robust for more than one use.

BRIEF DESCRIPTION OF DRAWINGS

The above-mentioned and other features and advantages of this invention, and the manner of attaining them, will become more apparent and the invention will be better understood by reference to the following description of embodiments of the invention taken in conjunction with the accompanying drawings, wherein:

FIGS. 2a and 2b are schematic drawings of an exemplary sterilization or use indicator.

DETAILED DESCRIPTION

The present disclosure relates to a sterilization and use indicator, which may provide indicia of the number of times a limited use device has been sterilized and/or used. A limited use device may be understood as a device that may be robust enough for more than one use, i.e., as dictated by mechanical design or even by regulatory approval. In an exemplary embodiment, the limited use device may be used more than once but less than 100 times, including all numbers and increments in the range of 2 to 100. The indicator may be applied to a limited use device on any surface that may be subject to sterilization.

In an exemplary embodiment, an indicator may include a series of membranes separating panels or cells containing numbers or other indicia, which may indicate the number of sterilization cycles. The membranes may be in pairs with one membrane in the pair breached or rendered permeable by, for example, exposure to a first environment, such as oxygen at room temperature. This membrane may otherwise be impermeable to oxygen at relatively higher temperatures or other gasses. The other membrane in the pair may be rendered permeable by a second environment, for example, exposure to oxygen at relatively higher temperatures (but not at room temperature or other gasses). It may be appreciated that relatively high temperature may be a temperature $T_1$ and the room temperature may be a temperature $T_2$, wherein $T_1 > T_2$. In some examples, room temperature may be in the range of 20° C. to 30° C., including all values and increments therein.

Therefore, one membrane in the outermost intact pair may be breached during use upon exposure to oxygen at room temperature and then, when the instrument is heated up and exposed to oxygen during, for example, the sterilization process, the other membrane in that pair may be breached upon exposure to oxygen at higher temperatures. Breaching of the membranes may allow the number in the panel or other indicia to indicate that an additional sterilization cycle has occurred. Following surgery, the instrument may be re-sterilized and the next pair of membranes may undergo a similar set of changes. The panels also may be reversed, wherein after use, one membrane in the outermost intact pair may be breached during sterilization and then, when the instrument is used at room temperature, the other membrane in that pair may be breached due to exposure to oxygen at room temperature. This may therefore allow the number in the panel or other indicia to indicate that an additional use has occurred. This proceeds in an incremental fashion until some preset number of cycles has occurred. Upon reaching the total number of uses or sterilization cycles, the indicia exposed by the membranes may then indicate that the instrument should no longer be used.

Figure 1:
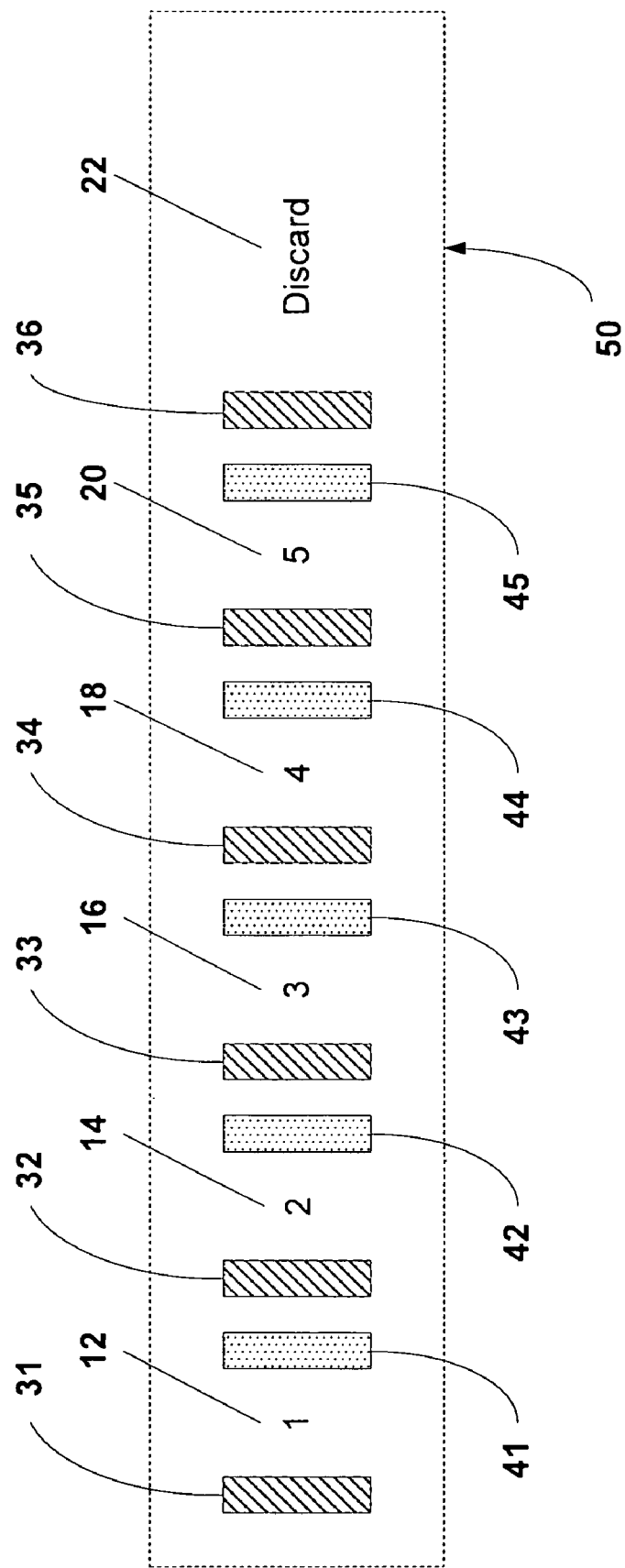
FIG. 1 is a schematic drawing of an exemplary sterilization or use indicator.

An example of an indicator is illustrated in FIG. 1. A series of cells 12, 14, 16, 18, 20, including indicia 1, 2, 3, 4, 5 may be provided on a substrate 50. The cells may include layers including membranes 31, 32, 33, 34, 35, 36 that may be breached by exposure to oxygen and high temperatures and layers including membranes that may be breached upon exposure to oxygen and room temperatures 41, 42, 43, 44, 45. As each pair of membranes are breached, the indicia and in this case, the number in the cells may change in a distinctive fashion so that it is visually obvious that the number of uses has been incremented. After the fifth sterilization cycle, the word "Discard" may be highlighted in the final cell 22.

Another embodiment may include the pairs of membranes in reverse order, i.e., wherein the outermost in the pair may be rendered permeable by oxygen and/or room temperature and the innermost in the pair may be rendered permeable by oxygen and/or elevated temperature. In addition, another embodiment may utilize some other atmospheric gas or compound other than oxygen, such as ethylene oxide. Furthermore, in another embodiment, a single membrane, rather than multiple membranes may be utilized between or around the number panels.

As illustrated in FIGS. 2a and 2b, membranes may be formed as windows in the layers and the indicia 12, 14, 16, 18, 20, 22 may be provided either on the second membranes 41, 42, 43, 44, 45 or on their own degradable membranes. As illustrated in FIG. 2b, as each membrane is exposed to an active environment E, i.e., an environment consistent with, for example, sterilization or use, the membrane may breach and the next membrane or indicia may be exposed.

Figure 3:
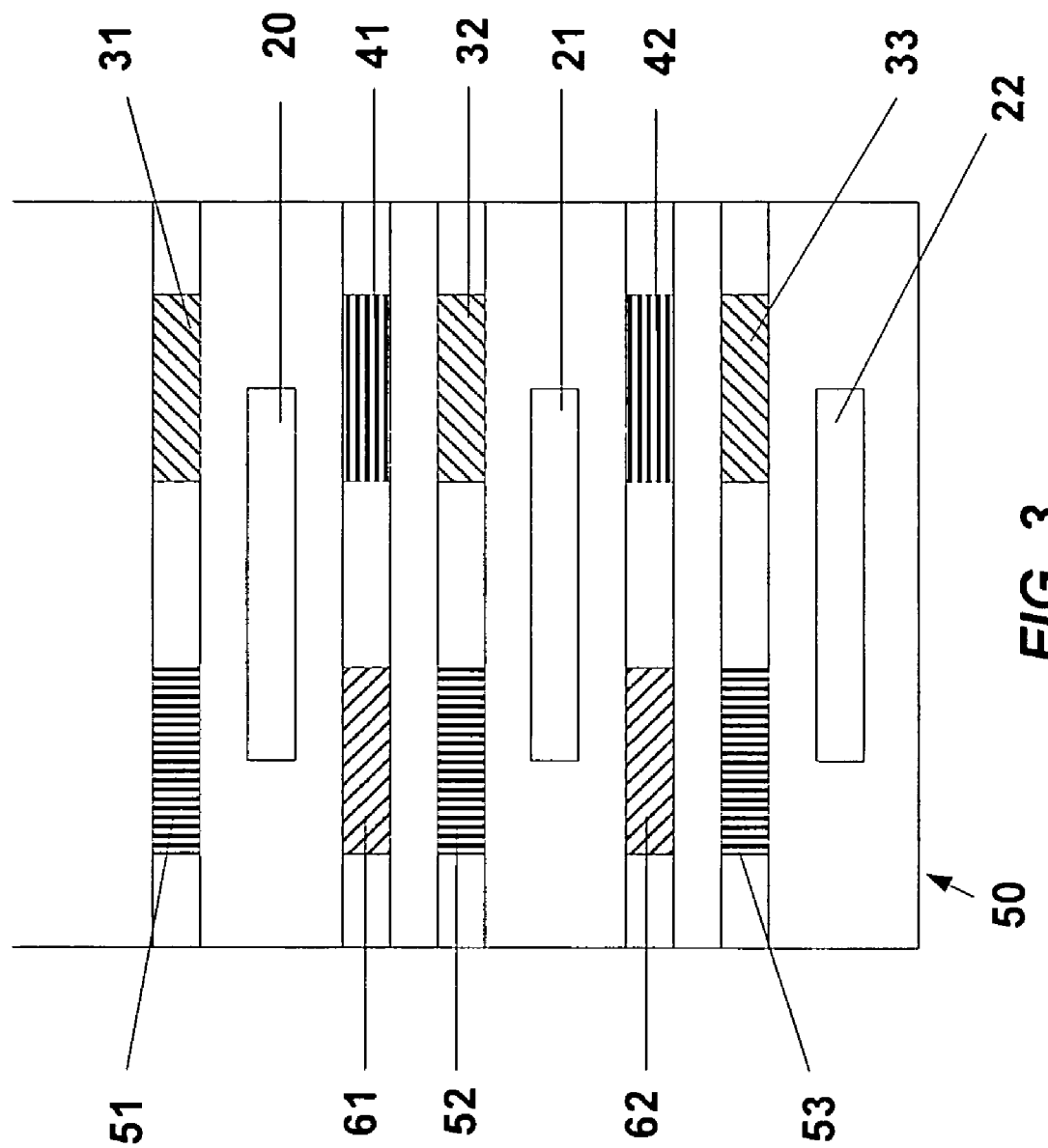
FIG. 3 is a schematic drawing of an exemplary sterilization or use indicator.

Furthermore, as illustrated in FIG. 3, rather than including a single membrane, each cell may include more than a single pair of membranes. For example, the first layer of a cell pair may include at least two membranes 31 and 51, or more, responsive to various types of sterilization, such as steam or ethylene oxide. Once exposed to an environment consistent with a given sterilization process, at least one of the windows may degrade, the indicia 20 may be exposed indicating a single sterilization. Upon use, the second layer of the cell pair may include membranes 41 and 61, which may be responsive to pH or ion levels of given fluids. Upon exposure to a given pH or ion level at least one of the membranes may degrade exposing the third layer of sterilization sensitive membranes. The process may iteratively repeat until the final indicia 22 is exposed or activated indicating that no more uses or sterilization cycles are available.

Breaching a membrane may be understood herein as rendering the membrane permeable, i.e., degrading the membrane such that an underlying layer or membrane may be exposed to the environment surrounding the initial membrane, or exposing a successive membrane to an environment to which a prior membrane may be permeable to. Thus, the membrane may be breached upon exposure to an environment consistent with sterilization or use. That is, the device need not be sterilized or used to breach a membrane, provided that the environment to which the indicator is exposed is relatively similar to that of sterilization or use.

The membranes herein may breach not only in the presence of oxygen, given temperatures, or other gasses, such as ethylene oxide, but may degrade in the presence of steam, liquids, ultraviolet (UV) radiation, or during plasma treatment. Liquids may include not only water, but liquids having specified pH levels or ion levels, including blood or other bodily fluids. It should be appreciated that these given environments may be present during sterilization or during use of the device. For example, sterilization may involve the presence of steam, ethylene oxide, acids, UV or plasma; whereas use of the device may involve the presence of various gasses or liquids, such as aqueous solutions, blood or other bodily fluids.

The membranes may therefore include a degradable or permeable polymer, wherein the polymer degradation or permeability may be triggered by the above mentioned triggering mechanisms, i.e., exposure to UV, exposure to steam or liquid at high or low temperatures, exposure to plasma treatments or exposure to various gasses. Degradable polymers contemplated herein, may include polyvinyl alcohol (PVOH), polylactic acid (PLA) based polyester terephthalate (PET), starch, cellulose, saccharides, PVA/PVOH, etc. Membranes permeable to oxygen may include, for example fluorosilicon acrylate or polymeric aliphatic acetylene. However, a number of other polymers or polymer additives may also be contemplated herein. Another embodiment may utilize a coating, plating, or other covering that may be breached or inactivated by exposure to sterilization or another given environment.

In addition, the membranes may have varying thicknesses. In a given indicator, at least one membrane may exhibit a first thickness that may be thicker or thinner than other membranes present in the indicator, exhibiting, for example, a second thickness. In addition, membranes exhibiting a third thickness or more thicknesses may be present. It may be appreciated that the varying thickness of the membranes may vary the exposure time necessary to breach the membrane. A relatively thicker membrane may result in a relatively longer exposure time for breaching or rendering permeable the membrane. In one example a membrane may have a thickness in the range of 100 nm to 1 mm, including all values and increments therein, such as in the range of 1 micrometer to 100 micrometers, 25 micrometers to 75 micrometers, 300 micrometers to 750 micrometers, etc.

The indicia may be numeric or non-numeric, representing the number of uses and/or sterilization cycles, and may include numbers, letters, words, symbols or a combination therefore. Furthermore, the indicia may not overtly indicate that the maximum number of sterilization cycles had been reached. Rather, there may be some other indicia of this occurrence using symbols such as a shape or design being completed, e.g., a pie may be filled by a number of pie pieces, or a number of dots may reach an indicated maximum level. In addition, it may be contemplated that such alpha-numeric indicators may not only change color, as alluded to above, but may be printed onto a degradable, i.e., breach-able panel or printed in a degradable ink on another membrane, such that the numeric or non-numeric indicator may replace one of or degrade in conjunction with a given membrane.

The indicator may be a provided on a substrate which may be affixed to the limited use device. The indicator may be affixed by mechanical means, such as a lip formed around a space for the indicator or a number of fingers protruding from the device for retaining the indicator to a surface, or the indicator may be affixed by chemical means, such as an adhesive composition. Additionally, the indicator may be integrated into the device, by forming the indicator directly onto a portion of the device. It is also contemplated that the indicator may be so integrated that if the indicator is removed, the device may be rendered inoperable.

Other means of indicia may be utilized as well in the indicator, for example tactile indicators (e.g. Braille dots, etc.), auditory indicators, magnetic indicators, electronic signals, etc. may be produced when the membranes are breached. In one exemplary embodiment, an electrical circuit may be completed upon the degradation of a membrane that may allow an auditory sound or electronic signal be produced.

Thus, the indicators contemplated herein may be applied to or integrally formed with a device, which may be used in a limited manner, i.e., the device may be used at least twice and up to about 100 times. The limited use device may be a medical device or other device, including surgical tools, dental tools, veterinary devices, etc.

Indicators formed herein may be formed in an environment inert to the membrane layers. Thus, where oxygen sensitive membrane layers are provided, the indicators may be formed in an inert gas such as nitrogen, argon or carbon dioxide reducing or substantially eliminating the presence of oxygen between the membrane layers. A first substrate layer may then be provided and indicia on the first substrate layer may be provided, wherein the indicia may indicate that, for example, the last use has occurred. Then over this layer multiple membrane and indicia layers may be formed. In addition, it is possible to first form the outer layers and then apply the substrate. Where adhesives are contemplated, the adhesive may be provided either before or after mounting the membrane and/or indicia layers to the substrate.

Thus, contemplated herein is a sterilization/use indicator for a limited use device. The indicator may include a plurality of layers, wherein each of the layers may comprise at least one membrane, and at least one indicia located between at least two of the layers, wherein each of the membranes may be configured to breach in response to exposure of the limited use device to a given environment, such as to an environment consistent with a sterilization or use of the limited use device.

Also contemplated herein is a limited use device, which may include a sterilization indicator including a plurality of layers, wherein each of the layers may comprise a membrane. The indicator may also include at least one indicia located between at least two of the layers. Each of the membranes may be configured to breach in response to exposure to an environment consistent with a sterilization or use of the limited use device to expose the indicia or another membrane.

Furthermore, contemplated herein is a method of indicating the number of sterilizations or uses of a limited use device. The method may include providing an indicator including a plurality of layers, wherein each of the layers may include at least one membrane. The indicator may also include at least one indicia located between at least two of the layers affixed to a limited use device. At least one of the membranes may be breached, exposing the indicia or another membrane upon sterilization or use of the device.

The foregoing description of several methods and an embodiment of the invention have been presented for purposes of illustration. It is not intended to be exhaustive or to limit the invention to the precise steps and/or forms disclosed, and obviously many modifications and variations are possible in light of the above teaching.

What is claimed is:

1. A sterilization/use indicator for a limited use device comprising:
   a plurality of cells in a series, wherein each cell comprises
      at least a pair of layers, wherein one layer of said pair of layers comprises a first membrane and the other layer of said pair of layers comprises a second membrane, and
      at least one indicia,
   wherein said first membrane degrades when exposed to a first environment and exposes said second membrane, and said second membrane degrades when exposed to a second environment, wherein said first and second environments are different and degrading said first and second membranes exposes a successive membrane in the next cell, providing an indicator of the number of times a limited use device has been sterilized and/or used.

2. The indicator of claim 1, wherein at least two of said layers are located between at least two of said indicia.

3. The indicator of claim 1, wherein each layer comprises at least two membranes.

4. The indicator of claim 1, wherein said indicator is provided on a first surface of a substrate.

5. The indicator of claim 4, wherein an adhesive is provided on a second surface of said substrate.

6. The indicator of claim 1, wherein said indicia comprises a visual indicator selected from the group consisting of numbers, letters, symbols, words and combinations thereof.

7. The indicator of claim 1, wherein said first environment and second environment are selected from the group consisting of a gas, temperature, liquid, steam, UV radiation, plasma and a combination thereof.

8. The indicator of claim 7, wherein said gas comprises ethylene oxide.

9. The indicator of claim 1, wherein said indicia includes a degradable material, wherein said material degrades upon exposure to a given environment selected from the group consisting of a gas, temperature, liquid, steam, UV radiation, plasma and a combination thereof.

10. The indicator of claim 1, wherein said indicia changes color upon exposure to a given environment selected from the group consisting of a gas, temperature, liquid, steam, UV radiation, plasma and a combination thereof.

11. The indicator of claim 1, wherein said first membrane exhibits a first thickness and said second membrane exhibits a second thickness, wherein said first thickness and said second thickness are different.

12. A limited use device comprising:
   a sterilization indicator including a plurality of cells in a series, wherein each cell comprises at least a pair of layers, wherein one layer of said pair of layers comprises a first membrane and the other layer of said pair of layers comprises a second membrane, and at least one indicia, wherein said first membrane degrades when exposed to a first environment and exposes said second membrane, and said second membrane degrades when exposed to a second environment, wherein said first and second environments are different, and degrading of said membranes of said pair of layers exposes a successive membrane in the next cell, providing an indicator of the number of times a limited use device has been sterilized and/or used.

13. The device of claim 12, wherein at least two of said membranes are located between at least two of said indicia.

14. The device of claim 12, wherein each layer comprises at least two membranes.

15. The device of claim 12, wherein said indicia comprises a visual indicator selected from the group consisting of numbers, letters, symbols, words and combinations thereof.

16. The device of claim 12, wherein said first environment and second environment are selected from the group consisting of a gas, temperature, liquid, steam, UV radiation, plasma and a combination thereof.

17. The device of claim 12, wherein said indicator is mechanically affixed to said device.

18. The device of claim 12, wherein said indicator is chemically affixed to said device.

19. The device of claim 12, wherein said indicator is integrally affixed to said device.

20. A method of indicating the number of sterilization cycles of a limited use device comprising:
   providing an indicator including a plurality of cells in a series, wherein each cell comprises at least a pair of layers, wherein one layer of said pair of layers comprises a first membrane and the other layer of said pair of layers comprises a second membrane, and at least one indicia; and
   exposing said first membrane to a first environment, degrading said first membrane and exposing said second membrane;
   exposing said second membrane to a second environment, wherein said first environment is different from said second environment, and degrading said second membrane; and
   exposing a successive membrane in the next cell and providing an indicator of the number of times a limited used device has been sterilized and/or used.

21. The method of claim 20, wherein each layer comprises at least two membranes.

22. The method of claim 20, wherein said first and second environments are selected from the group consisting of a gas, temperature, liquid, steam, UV radiation, plasma and a combination thereof.

23. The method of claim 20, further comprising degrading said indicia upon exposure to a given environment selected from the group consisting of a gas, temperature, liquid, steam, UV radiation, plasma and a combination thereof.

24. The method of claim 20, wherein said first and second environments are different from a third environment for degrading said indicia.

25. The method of claim 20, further comprising providing at least two of said membranes between at least two of said indicia.

* * * * *